United States Patent [19]
Siegel et al.

[11] Patent Number: 6,142,779
[45] Date of Patent: Nov. 7, 2000

[54] BREAKAWAY DEVICES FOR STABILIZING DENTAL CASTS AND METHOD OF USE

[75] Inventors: Sharon Crane Siegel, Eldersburg; Ronald Bruce Gunderson, Silver Spring, both of Md.

[73] Assignee: University of Maryland, Baltimore, Baltimore, Md.

[21] Appl. No.: 09/426,771

[22] Filed: Oct. 26, 1999

[51] Int. Cl.[7] .................................................. A61C 11/00
[52] U.S. Cl. ....................................................... 433/60
[58] Field of Search ............................... 433/54, 60, 64, 433/213

[56] References Cited

U.S. PATENT DOCUMENTS

| | | | |
|---|---|---|---|
| 2,751,909 | 6/1956 | Weitzner . | |
| 4,382,787 | 5/1983 | Huffman . | |
| 4,786,253 | 11/1988 | Morrais | ...................................... 433/60 |
| 5,482,460 | 1/1996 | Farnor, Jr. et al. | .................... 433/60 X |
| 5,658,143 | 8/1997 | Kuperman | ................................. 433/60 |
| 5,934,901 | 8/1999 | Huffman | ............................... 433/60 X |

OTHER PUBLICATIONS

"Principles, Concepts, and Practices in Prosthodontics—1994", Academy of Prosthodontics, The Journal of Prosthetic Dentistry, vol. 73, No. 1, Jan. 1995, pp. 73–94.

Stephen F. Rosenstiel et al., "Contemporary Fixed Prosthodontics", Second Edition, Treatment IX (Fig. 30–33).

M.A. Freilich, DDS et al., "Principles for Selecting Interocclusal Records for Articulation of Dentate and Partially Dentate Casts", The Journal of Prosthetic Dentistry, Aug. 1992, vol. 68, No. 2, pp. 361–367.

Herbert T. Shillingburg, Jr., DDS et al., "Fundamentals of Fixed Prosthodontics", Third Edition, Chapter 5, "Articulation of Casts", pp. 47–72.

Robert G. Craig, Ph.D., "Restorative Dental Materials", Ninth Edition, Chapter 12, "Gypsum Products and Investments", pp. 336–361.

*Primary Examiner*—Nicholas D. Lucchesi
*Attorney, Agent, or Firm*—Burns, Doane, Swecker & Mathis, L.L.P.

[57] ABSTRACT

A device for efficiently, accurately and consistently securing dental casts while an articulator is attached thereto includes a spine connecting a first stabilizing pad at one end to a second stabilizing pad at an opposite end. The device includes a breakaway feature which allows a connection between the casts to be broken with manual force. The first stabilizing pad and the second stabilizing pad are secured to maxillary and mandibular casts with an adhesive or the like, or by other methods such as magnets, to create a rigid connection between the accurately related maxillary and mandibular casts. The breakaway feature allows a technician to easily break the connection between the maxillary and mandibular casts with manual force after the articulator has been attached to the casts.

38 Claims, 4 Drawing Sheets

BREAKAWAY DEVICES FOR STABILIZING DENTAL CASTS AND METHOD OF USE

BACKGROUND OF THE INVENTION

1. Field of the Invention

The present invention relates to systems and methods for accurately stabilizing dental casts. More particularly, the present invention relates to a bracing device which temporarily secures accurately related maxillary and mandibular casts while an articulator is connected thereto and methods of stabilizing dental casts during such an operation.

2. Brief Description of the Related Art

Dentists and dental technicians frequently make dental stone casts (including diagnostic casts, working casts and master casts) which represent the patient's mouth at various stages in the clinical procedures of diagnosis and restoration. It is often necessary to place these casts on a mechanical device called an articulator that allows for a simulation of the functional relationship of the jaws, and reproduces the movements of the lower jaw (mandible). The first step in this process is to relate or position the upper cast (representing the patient's maxilla or upper jaw) on the articulator, attached with a rigid setting plaster. The lower cast (representing the patient's lower jaw or mandible) is next oriented on the articulator by relating it to the mounted upper cast. The lower cast is related to the upper cast either in a determined intercuspating relationship or through the use of a recording material, e.g., a wax or elastomeric material, placed between the patient's teeth (or between wax rims and record bases simulating future positions of denture teeth) to create a record which is then transferred to the articulator and used to position or relate the lower cast to the upper cast. This process results in a very specific positioning of the casts on the articulator in a mechanical relationship that is the same as the functional relationship of the teeth in the patient's mouth and the joints which are responsible for the functional movements of the jaw (the temporomandibular joints). These articulated stone casts are used in many ways by the dentist but most frequently are used by the dentist, student dentist or dental technician to make a prosthesis or restoration for the patient (an implant supported restoration, a crown or cap, a fixed partial denture or bridge, a removable partial denture or partial plate, or a complete denture or plate). The restoration that is made from the articulated casts must meet or occlude correctly when placed into the patient's mouth and the restoration or prosthesis must function properly against the opposing teeth and in all of the movements that the patients jaw can make. This must be accomplished such that the restoration is in harmony with the muscles of mastication (chewing muscles), temporomandibular joints (jaw joints), and the existing occlusion (bite) to allow the patient to masticate (chew) and phonate (speak) properly.

Virtually every dentist, student dentist and dental technician has experienced the consequences of improperly related casts because of the difficulty, awkwardness, lack of standardization, or ineffectiveness in relating casts using current procedures. Currently, there are at least three major concerns that need to be resolved in providing a procedure for relating the mandibular cast to the maxillary cast that will result in an improvement in the articulation process. The first concern addresses the need to develop a process that is consistently accurate regardless of the variables of recording material or mounting materials used to relate and attach the mandibular cast to the articulator. The second is to develop a process that is cost effective and efficient to use so that the procedures will be universally applied. The third is to have a set of procedures that may be conveniently accomplished by one person.

In order for the procedures to produce a consistently accurate articulation of the mandibular cast, the cast must be rigidly attached to the mounted maxillary cast when the plaster is applied to attach the lower cast to the articulator. One reason that it is necessary to rigidly secure the casts is that the plaster used to attach them to the articulator expands by a certain percentage during the setting process. This percentage expansion will vary with the material chosen. This expansion potentially changes the relationship of the casts to each other if the casts are not rigidly secured together. A second significant reason that the cast should be rigidly attached is to eliminate inadvertent movement of the cast during the plaster application procedure. The mandibular cast may be easily displaced from its relationship to the upper mounted cast as highly viscous mixed plaster is loaded onto the base of the lower cast and the articulator is closed onto the plaster to establish the articulation.

The resulting alteration in the correct relationship of the casts from either or both of the above two causes is particularly significant when the patient does not have adequate teeth that allow the dentist or technician to easily correlate and verify the intercuspating (interdigitating) position of the teeth or if significant numbers of teeth have been prepared for crowns, bridges, etc. so that the occluding (biting) surfaces of the casts can be positioned only by using an interocclusal record (made in the patients mouth and then transferred in between the casts to record the position of the patient's upper jaw or teeth to the lower jaw or teeth). In these situations it may be very difficult to verify the resulting accuracy of the articulation by visual inspection and the fabrication procedures for the restoration or prosthesis would then proceed with the casts relating in an inaccurate manner. Improperly related casts will result in a restoration or prosthesis (crown, bridge, denture) being made that has improper functional occlusion. This will prevent the opposing teeth from contacting properly and can potentially introduce pathologic forces onto the teeth and supporting bone. If the restoration is not properly adjusted, the result could include tooth mobility or loosening for the patient, bone loss around the tooth, muscle pain, and/or temporomandibular joint dysfunction (TMD). To avoid these very serious problems resulting from improper occlusion, the dentist must spend extra time with the patient adjusting the restoration. This increases the cost of the restoration to the dentist, often results in altering the treatment schedule, and requires the patient to remain in the dental chair for an extended period of time. The patient may make the assumption that the dentist is not competent or efficient in his or her prosthodontic treatment procedures as a result of this experience. The potentially negative impact of this perception on the dentist's practice and patient relations may be significant.

Another problem encountered in the articulation process is that the adhesives currently used for the purpose of securing casts together do not stick to wet or moist casts. This condition further introduces potential error in the cast relationship and adds significant time to the articulation process. The adhesive materials most commonly used to attach casts together require that the cast must dry for approximately 24 hours before the adhesive materials are applied. These traditionally used materials have further difficulty in sticking to the casts because the stone casts are porous, holding water and contaminants on the surface. The requirement for a thoroughly dry cast adds a day to the time that is required before the technician can begin to fabricate the restoration.

Another issue to consider is the need for improving the efficiency and cost effectiveness of the process of articulation. The current state of the art of relating casts together and stabilizing them is to use rigid or semirigid materials available in the laboratory or office area (pieces of broken tongue depressors, cotton tip applicators, nails, burs or bur shanks, metal rods, Popsicle® sticks, match sticks, paper clips, etc.) which are then attached to each cast using sticky wax, gray stick compound, or glue from a glue gun. Most of these materials do not adhere to wet or moist casts and none of them adhere with strength to wet or moist casts. In order to get a strong bond, a waiting period of at least a day is required to be assured that the unbound water in the stone cast has completely evaporated. Dental technicians and dentists have been known to use rubber bands wrapped around the casts to secure the relationship as the casts are placed on the articulator even though the rubber bands are elastic and do not hold a secure, rigid relationship. There are some advocates of using a technique of holding the casts together whereby the hand holds the casts while the plaster used to secure them to the articulator sets. This is a time wasting procedure of questionable practicality when a large number of casts are to be articulated by the dentist or technician.

Yet another consideration is to provide a process of articulation that is practical and efficient for one person to accomplish. The process of securing casts together can be an awkward procedure for the dentist, student dentist or technician to perform without additional assistance from a second person. The procedure is accomplished by the dentist, student dentist or technician holding the casts together with one hand while applying the wax, etc., to the casts with the other hand, all while maintaining control of the articulator in some manner, frequently by holding it between the elbow and body. This process alone can lead to errors that may not be detected until the restoration is completed and returned to the patient's mouth for clinical evaluation. It has long been evident to clinicians practicing prosthodontics that there is an established need for an easier, neater, more efficient, more predictably accurate way to secure the casts together, one that can be done very soon after the casts set to allow the restoration to be fabricated as soon as possible, and one that may be accomplished easily and accurately by one person.

SUMMARY OF THE DISCLOSURE

In one aspect, the present invention relates to an inexpensive brace for efficiently and consistently securing accurately related maxillary and mandibular casts. The brace includes a spine having first and second ends. The spine connects a first pad at the first end and a second pad at the second end. The first and second pads are securable to the maxillary and mandibular casts to create a connection between the maxillary and mandibular casts. Preferably, a tab extends from the spine so that a dentist or technician can manipulate the brace. A brace according to the present invention also includes a breakaway feature which yields to manual pressure, thereby releasing the connection between the maxillary and mandibular casts, after the plaster securing them to the articulator has set.

Another aspect the present invention includes an adhesive system that adheres to wet or moist surfaces. Such an adhesive system is greatly needed in order to save time in the fabrication of the restoration. The reduced time in laboratory procedures would increase the efficiency for the laboratory, make the dentist's practice more efficient, and potentially result in a more satisfied customer. In addition, using an adhesive that is effective on wet or moist casts provides more assurance that the stabilization is accurate even if the procedure is done before the casts are totally dry.

In a first exemplary embodiment the spine includes a center portion which is wider than its end portions. In the first embodiment the breakaway feature includes notches defined both between the first pad and the wide center portion, and between the second pad and the wide center portion of the spine. After an articulator has been attached to the braced mandibular and maxillary casts, a technician can break the spine by applying a force to the tab and twisting the spine. Stress caused by the applied pressure is concentrated at the notches in the spine, causing the spine to break near the notches and breaking the connection between the casts.

In a second exemplary embodiment, the breakaway feature includes necked portions of the spine. The necked portions are located near the areas where the spine is connected to the first pad and the second pad. As in the first embodiment, a technician can easily break the spine by applying force to twist the tab. Stress caused by the applied force is concentrated at the neck portions, causing the spine to break away from the one of the first and second pads, thereby breaking the connection between the maxillary and mandibular casts.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DETAILED DESCRIPTION OF PREFERRED EMBODIMENTS

Figure 1:
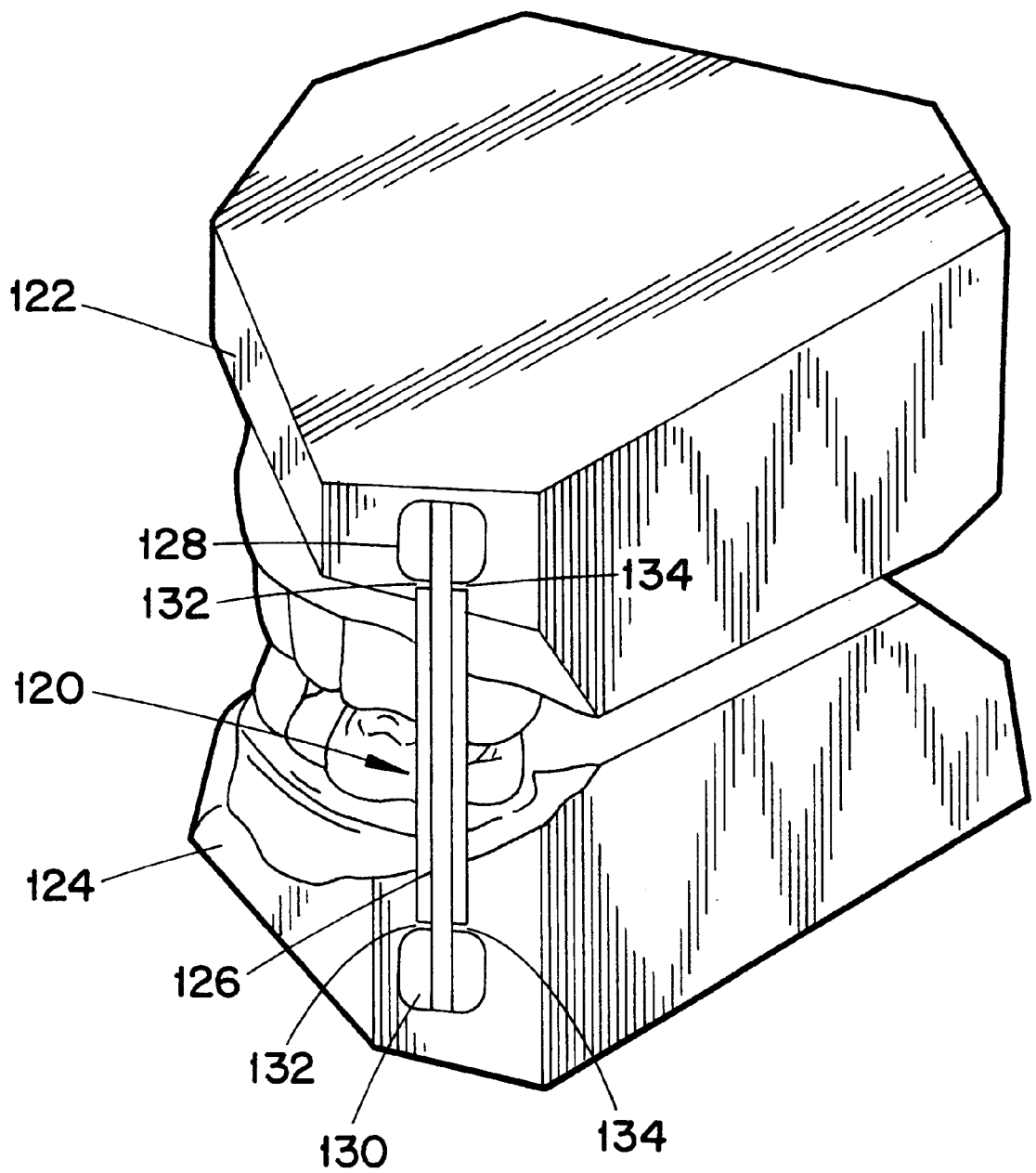
FIG. 1 is a perspective view of maxillary and mandibular casts being secured by an embodiment of the present invention.

A breakaway device for stabilizing dental casts according to the present invention resolves the above-discussed problems. Preferably a device in accordance with the present invention includes a rigidly designed spine with two or more flat pad attachments (which may be round, square, oblong, or any shape that is slightly larger than the width of the spine) on each end to prevent the spine from rotating on the base of the cast and providing a broad surface area for an adhesive to attach to the cast. Preferably, a device in accordance with the present invention is injection molded as an integral component to minimize fabrication costs. Such devices are convenient and readily available for the dentist, student dentist or dental technician to use, as opposed to the inconvenience of having to find a suitably rigid object (usually not well adapted for securing wet or moist casts together) lying around the office or the laboratory. Adding to the efficient use of a brace according to the present invention is an adhesive system associated with the stabilizing device or brace.

Additionally, the dentist or technician may use the system more easily and with greater accuracy because the adhesive system allows the dentist or technician to perform the stabilization with only one hand as the adhesive can be incorporated as an integral part of the brace. Braces in accordance with the present invention contrast with the existing techniques, where one hand must hold the stick and casts together and the other hand is used to apply the sticky wax, compound, etc., while balancing the articulator between the user's elbow and body.

Braces, in accordance with the present invention, preferably include one or more of several features that make it unique, efficient and valuable for securing casts together. These features include: 1) a rigid, disposable spine element; 2) a breakaway feature to make removal of the stabilizing brace from the cast efficient and easily accomplished without the need for additional tools or instrumentation, e.g., a knife or scalpel blade, and which preferably retains the adherent attachment segments at the ends of the stabilizing device onto the casts as a quality assurance feature for the dental laboratory to identify that stabilization was used in the articulation process; 3) in some embodiments, an adhesive system that attaches to moist casts and that is either a component of a brace, a packaged kit or is attached to the attachment segments of the device; and 4) an imprint of initials, symbols, or the like, on the segments of the device which are left attached to the cast indicating that stabilization of the casts had been performed and accomplished.

A stabilizing device according to the present invention solves a number of the problems identified with the articulation procedures. It makes the procedure of making dental prostheses (crowns, bridges, and dentures) easier, more time efficient, and less costly for the dentist, the dental technician or dental laboratory. It provides to the dentist, dental school, dental student, dental laboratory or dental technician a specifically designed, readily available product to accomplish the cast stabilization procedure that is neat and efficient to use and can be provided in a convenient package or kit with an appropriate adhesive and applicator. It insures that the casts are secured together with consistent accuracy and ease as the adhesive attaches the device to either wet, moist or dry casts. Furthermore, attachments can be accomplished easily by one person.

Accurate and consistent stabilization of the maxillary and mandibular casts, achievable by braces in accordance with the present invention, as they are attached to the articulator, significantly contributes to the fabrication of a restoration that is properly related to the patient's oral function, eliminating or greatly reducing the need for the dentist to use valuable chair time to adjust the restoration into the proper occlusion. A device in accordance with the present invention decreases the time the patient is in the dental chair, which is of great comfort to many patients. A device in accordance with the present invention helps to insure the patient's comfort in that the functional, biting surface of the restoration will be fit more accurately against the opposing teeth. A device in accordance with the present invention minimizes patient complaints from any post-operative complaints that may result from an improperly adjusted restoration. A device in accordance with the present invention increases the efficiency for the dental laboratory in that the casts can be related, stabilized with accuracy, and expediently articulated in a timely manner since the adhesive attaching the stabilizing device can be applied to a wet or moist cast. Furthermore, a device in accordance with the present invention makes the procedure of separating the stabilization device easier due to the breakaway feature, which requires no extra equipment to remove the stabilizing segments. Preferably, the stabilizing segments or pads retained on the surface of the cast can have a surface identifier (or other appropriate logo/identifying initials) as a signature of quality assurance of the laboratory to the dentist that the casts were stabilized prior to fabricating the restoration.

Preferably, the upper surface of each of the stabilizing brace's pads includes letters, symbols, or the like, which act as an indicator that stabilization has been properly accomplished with the stabilizing brace. An attachment surface of the pads can be roughened or smooth, and can include undercut retentive features as needed to provide an ideal surface for adhesive attachment to the casts.

Any letter, letters, number, numbers, symbol, symbols, or combination thereof may be used on the brace to indicate stabilization has been properly performed. A breakaway feature, which allows the central portion of the brace to separate from the stabilizing ends of the spine, is included in the stabilizing device. This feature can be located at the juncture of the central body or spine of the stabilizing brace and the stabilizing attachment ends or pads of the brace, but may be positioned anywhere along its length. It preferably includes a lever or similar extension for easily applying a force, including torque, shear, and other forces, to the brace. This extension will be of a size and shape that will allow the dentist, dental student or laboratory technician to snap, or easily break, the stabilizing brace from a cast to which it had been secured, leaving the adhesive pads attached to the cast with a lettered, numbered, or symboled identifier on the pads for the indication that the stabilizing brace has been used for stabilization.

Turning now to the drawing figures, exemplary embodiments of apparatus and methods in accordance with the present invention will now be described. Like reference numerals designate identical or corresponding elements throughout the several figures. An exemplary stabilizing device or brace 120 is shown in use in FIG. 1. The brace 120 connects a maxillary cast 122 and a mandibular cast 124. A spine 126 connects a first stabilizing pad 128, which is securable to the maxillary cast 122, and a second stabilizing pad 130, which is securable to the mandibular casts 124. With the pads 128, 130 secured to the casts 122, 124, the accurately related casts 122, 124 remain in their relative positions while an articulator is attached to the casts. The brace 120 can include notches 132, 134, cutaway portions, or the like to weaken the spine 126. Notches 132, 134 therefore provide brace 120 with a breakaway feature or element, so that a brace 120 secured to a set of casts can be readily broken or fractured by a user to separate the casts.

Figure 2:
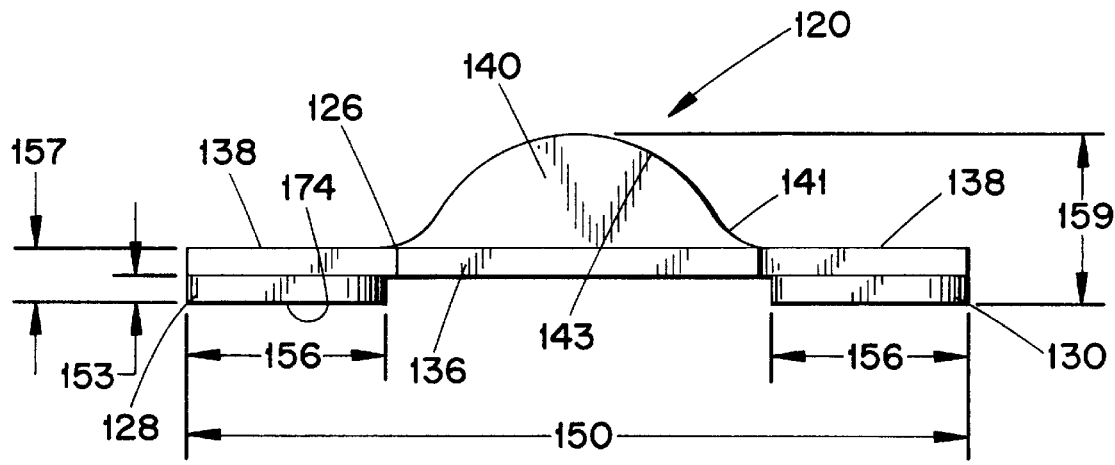
FIG. 2 is an elevation view of a first embodiment of the present invention.
Figure 3:
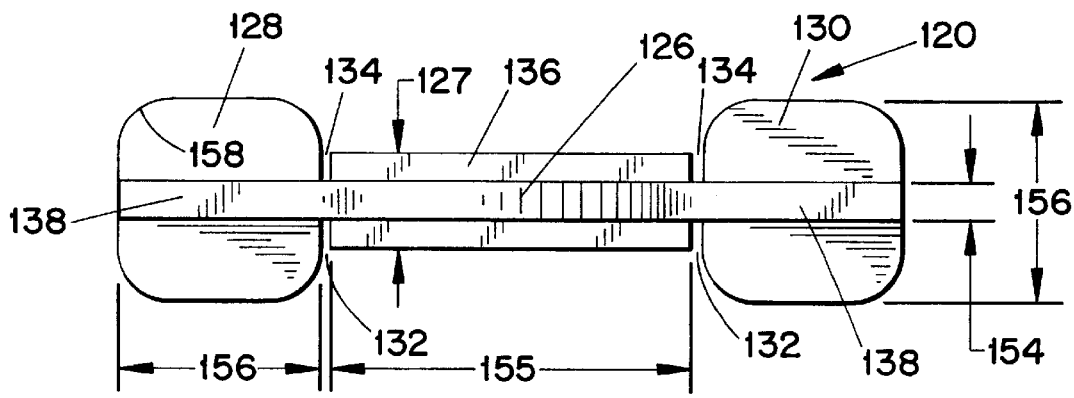
FIG. 3 is an is a top plan view of the first embodiment.
Figure 4:
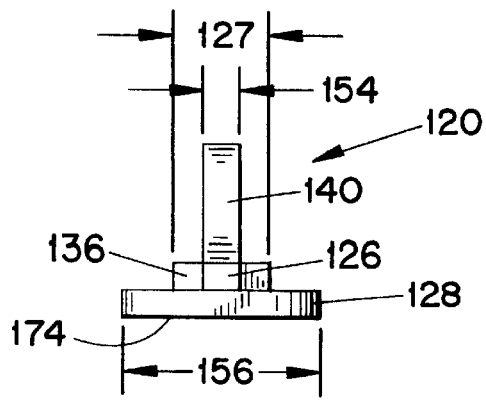
FIG. 4 is an end view of the first embodiment.

In a first exemplary embodiment shown in FIGS. 2–4, brace 120 includes the first pad 128 and the second pad 130 connected by the spine 126. The pads 128, 130 are spaced from one another along the spine 126 at a distance appropriate for attaching the first pad 128 to the maxillary cast 122 and the second pad 130 to the mandibular cast 124.

In the first embodiment, the spine 126 includes a wide center portion 136 which is wider than end portions 138 attached to the pads 128, 130. The wide center portion 136 defines notches 132, 134 both between the first pad 128 and the spine 126 and between the second pad 130 and the spine 126. The wide center portion 136 has a width 127, preferably about 7 mm. A tab 140 extends from the spine 126 and provides a convenient location for a technician to manipulate the spine 126 to apply force to the spine 126 to snap, fracture, or otherwise break the spine 126. Preferably, the tab 140 has radiused end portions 141 and radiused center portion 143. Preferably, the radiused ends 141 have a radius of about 5 mm, and the radiused center portion has a radius of about 12 mm. Additionally, the tab 140 may optionally include a single or pair of depressions or concavities on the lateral face(s) thereof to facilitate placement of a finger of a user on the spine 126 of the brace 120.

Figure 5:
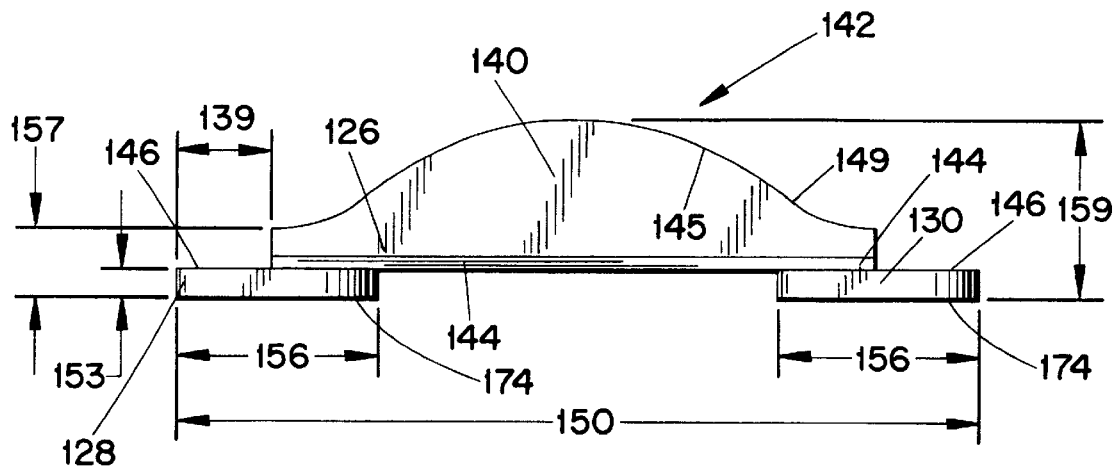
FIG. 5 is an elevation view of a second embodiment of the present invention.
Figure 6:
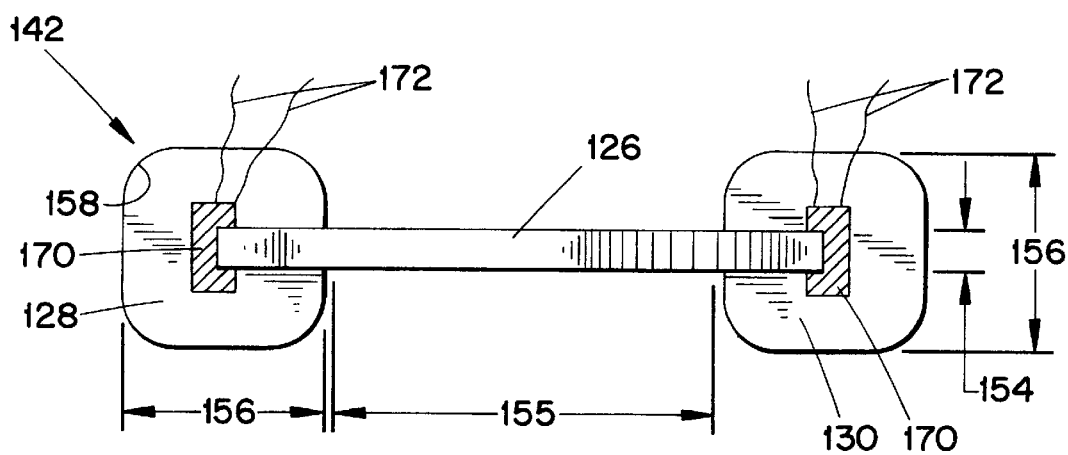
FIG. 6 is a top plan view of the second embodiment.
Figure 7:
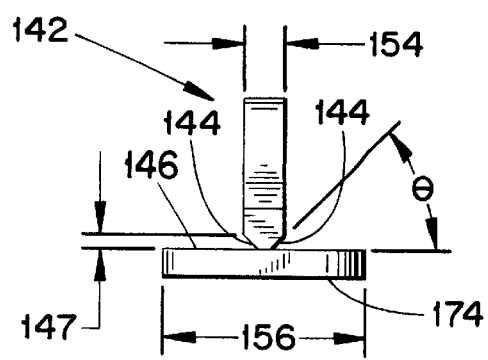
FIG. 7 is an end view of the second embodiment.

FIGS. 5–7 illustrate a second embodiment of a brace 142 in accordance with the present invention. Brace 142 includes pads 128, 130 connected together by a spine 126 having a necked-down portion or portions 144. The pads 128, 130 are connected to define an overhanging portion 139 of each pad 128, 130 that extends beyond the ends of the spine 126. Preferably, the overhanging portion 139 extends about 7.5 mm beyond the end of the spine 126. A tab 140 is generally coextensive with the spine 126 and preferably includes radiused center and end portions 145, 149. Preferably, the radiused center portion 145 has a radius of about 25 mm and the radiused end portions 149 have radii of about 10 mm. The necked-down portion or portions 144 are created by tapering the spine 126 at an area where the spine 126 meets the pads 128, 130, as can be appreciated from FIG. 7. Preferably, the necked-down portion or portions 144 taper over a distance 147 of about 1 mm from a top surface 146 of the pads 128, 130. The spine 126 is tapered at an angle θ from the top surface 146 of the pad or pads 128, 130 to create a narrow interface (or decreased shared surface area) between the pads 128, 130 and the spine 126. Angle θ is preferably between about 30° and about 70°, and more preferably θ is about 50°.

The necked-down portion or portions 144 creates a weakened area where the spine meets the pads 128, 130. Necked-down portion or portions 144 form regions of relative weakness of spine 126, and thus are the portions of device 120 which fracture first when a force is applied to the spine 126. In this regard, the remaining portions of the spine 126 are constructed to be stronger than necked-down portion or portions 144, so that a fracture at least initiates in these necked-down portions, causing brace 142 to break in a predictable manner. Thus, the necked-down portion or portions 144 act as a breakaway element, allowing the brace 142 to be easily and predictably broken with manual force.

A stabilizing device or brace in accordance with the embodiments of the present invention, shown in FIGS. 2–7, has a length 150 ranging between about 30 mm and about 70 mm, with the length 150 preferably between about 40 mm and about 60 mm. While the first and second embodiments illustrated include flat surfaces, one or more of the surfaces of the brace may have some convexity, concavity, or roundness to improve the esthetics of the device. A thickness 154 of the spine 126 can range from about 0.5 mm to about 10 mm, with a preferable thickness of about 3–4 mm. Part of the thickness can be created by the wide center portion 136. The pads 128, 130 at both ends increase the surface area for securing the two casts 122, 124 together. The size of this increased area can be any size with the preferable shape being a 20 mm circle or two 15 mm×15 mm extensions. The pads 128, 130 at both ends of the brace may be any shape, round, square, rectangular, pentagonal, etc. While one of ordinary skill in the art will readily appreciate that a distance 155 between pads 128, 130 can be selected over a wide range to accommodate cast separation distances from pediatric to adult sizes, preferably the distance 155 is between about 10 mm and about 55 mm, more preferably 40 mm, and most preferably about 35 mm.

As in the embodiments shown in FIGS. 2–7, pads 128, 130 preferably are geometrically square and have a square dimension 156 of about 15 mm. Preferably, pads 128, 130 have radiused corners 158 having a radius of 4 mm. Pads 128, 130 have a preferred height 153 of about 2 mm. Both the pads 128, 130 and the spine 126 together have a preferred total height 157 of about 4 or 5 mm. The overall height 159 of braces 120, 142 in the first and second embodiments is preferably about 13 mm.

Pads 128, 130 can be secured to the casts with an adhesive system designed for use with wet or moist cast material. Generally, dental cast material is a gypsum product. The chemical make-up and physical properties of gypsum products used in dental casts are discussed in detail in Chapter 12 of the text *Restorative Dental Materials* by Robert G. Craig (9th ed. 1993) which is herein incorporated by reference.

Adhesives that can be used to secure the stabilizing brace to the cast preferably bond to a wet or moist cast, so that the brace can be employed earlier in the process of the casts drying than prior methods. Examples of suitable adhesive systems include, but are not limited to, cyanoacrylates (e.g., Maxicure or Instacure, Bob Smith Industries, Atascadero, Calif.), including both gels and liquids, both with fillers and without fillers, glues used in a glue gun both with and without accelerators, sticky wax, gray stick compound, impression compound, polyethylene, Elmers® Glue (Elmers Products, Inc., Columbus, Ohio), epoxies including marine epoxies such as rapid set Marine-Tex Epoxy (ITW Philadelphia Resins, Montgomeryville, Pa.), adhesive tapes, spray adhesives such as 3M's Super 77 (3M Company, St. Paul, Minn.), resins including marine resins, creeping crack cure, or an acetone and polyvinyl resin such as Multibond Adhesive (Beacon Chemical Company, Mt. Vernon, N.Y.). A marine-type adhesive is preferably utilized for its ability to bond in the presence of water. Examples of marine-type adhesives include the Maxicure cyanoacrylate used with Instaset accelerator (Bob Smith Industries, Atascadero, Calif.) and the Marine-Tex dual system adhesive.

The adhesive system is preferably pre-applied by the manufacturer to the bottom surface 174 of pads 128, 130, so that the device can be secured to casts to stabilize the casts, as described above. Alternatively, the adhesive system can be applied just before securing the brace 142 to the casts.

Figure 8:
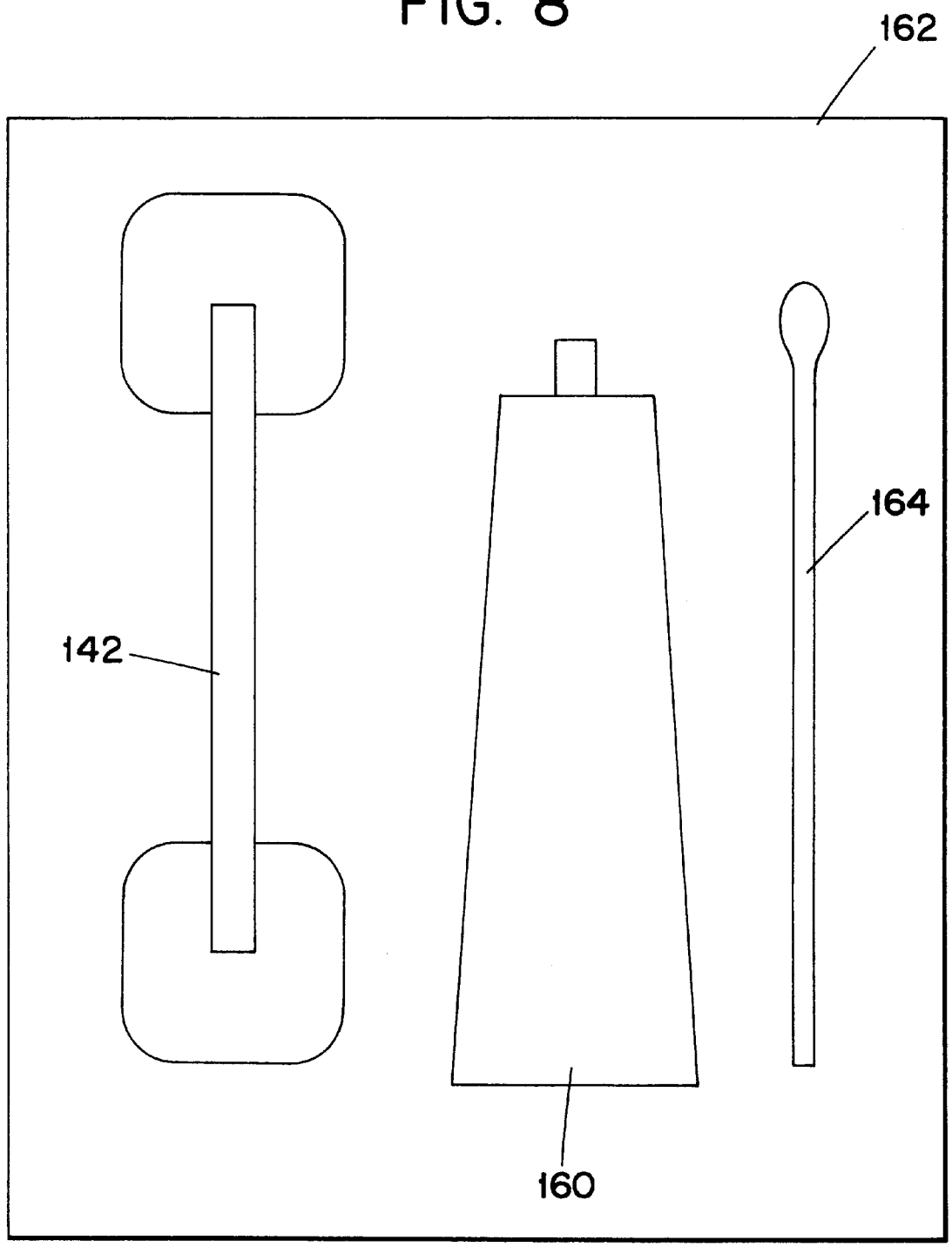
FIG. 8 is a diagram of a kit according to the present invention.

As seen in FIG. 8, a container of an appropriate adhesive 160 can be combined in a package 162 along with an applicator 164, if necessary, and a brace 142 in a kit, thus conveniently providing the components necessary to secure dental casts. Alternatively, the adhesive can be applied to the brace 142 by a manufacturer and covered by release paper. When the casts are ready to be secured, the release paper is peeled off to expose the pre-applied adhesive and the brace 142 is secured to the casts.

The surface area of bottom surface 174 of pads 128, 130, the particular adhesive system, and the strength of the breakaway clean used are selected together so that the bond strength between the pads and the casts is greater than the force necessary to fracture or break the breakaway element. The co-design of these features helps ensure that the breakaway feature properly allows stabilizing braces in accordance with the present invention to stabilize casts, while permitting the casts to be easily later separated.

In the alternative, the pads may be secured to the dental casts with magnets or magnetic material 170 (see FIG. 6). Magnets or magnetic material 170 can be incorporated into the pads, or the pads themselves can be formed of the magnetic material 170. The magnets or magnetic material 170 in the pads correspond to magnets or magnetic material contained or embedded in the upper and lower dental casts (not illustrated) which have polarities so that the magnetic material 170 of the pads will be attracted to the magnetic material in the casts. The magnetic material 170 can be traditional magnetics such as rare earth magnets. Alternatively, an electromagnetic can be used as magnet 170 for which appropriate electric leads 172 are provided to place the coil or coils in electrical communication with an appropriate source of electrical energy (not illustrated) to energize the coil and magnetically secure the brace 142 to dental casts. Other means of securing the brace 142 of the present invention are also within the scope of the invention.

A dentist or dental technician can secure accurately related mandibular 124 and maxillary casts 122 during the application of an articulator by using braces in accordance with the present invention. The technician secures one of the pads 128 130 to the maxillary cast 122 and the other of the pads 128, 130 to the mandibular cast 124 once the casts 122, 124 have been properly related. The spine 126 connecting the pads 128, 130 prevents relative movement between the two casts as the articulator is attached thereto. Once the articulator has been secured to the casts the technician can release the connection between the pads by manipulating the tab 140 to produce a twisting, shearing, or other force on the spine. As the manual force is applied, the spine 126 will break at the breakaway features, e.g., notches 132, 134, neck 144, or the like, thus allowing the casts 122, 124 to be articulated.

In an embodiment including magnetic breakaway features, magnets or magnetic materials, including ferromagnetic materials including iron and iron alloys, are prepositioned in, or incorporated into, the wet casting material. Magnets 170 incorporated into the pads 128, 130 of a brace, according to the present invention, have polarities opposite the magnetic material in the casting material. When the casts are to be separated, the magnetic pads are moved out of alignment with the magnetic portions of the casts, thereby releasing the casts. Alternatively, when the magnetic elements 170 are electromagnets, the electro-magnets can be de-energized, thus releasing the device from its magnetic attraction to the casts. Thus, braces including magnetic pads are reusable to hold additional casts, as described above.

As will be readily appreciated by one or ordinary skill in the art, breakaway devices in accordance with the present invention can include only one breakaway element, so that the device can be broken into only two pieces. If the fractured pieces need to be further trimmed of a portion of the device after being broken apart at the breakaway element, the user can trim the pieces using known devices and methods, such as shears. Alternatively, breakaway devices for stabilizing dental casts in accordance with the present invention can include two breakaway elements, as described in greater detail herein, so that no further work on the fractured device is necessary after being broken. Of course, more than two breakaway elements incorporated into a stabilizing device is also within the spirit and scope of the present invention.

The stabilizing brace can be fabricated from any suitable material which is strong and moderately rigid, so that the brace will stabilize dental casts when secured thereto. Examples include, but are not limited to, wood, metals and metal alloys such as steel and stainless steel, plastics, composites, ceramics, vinyls, acrylics, fiberglass, cardboard, plywood, paper, tile, brick, concrete, fabric, glass, rope, impression plaster, stone, multicellular synthetic resins such as Styrofoam® (Dow Chemical Co., Midland, Mich.) and polymethacrylate resins, such as Duralay Resin (Reliance Dental Manufacturing Co., Worth, Ill.), G.C. Pattern Resin (G.C. Corporation, Tokyo, Japan), or Lucite® (ICI Acrylics, Inc., Cordova, Tenn.). Preferably, the brace is injection molded as a single, integral, monolithic piece, for which materials that are capable of being injection molded are preferred.

Accordingly, the present invention provides a stabilizing device or brace and a method of use which improves the efficiency, consistency and accuracy of a commonly performed, and many times awkward, dental procedure. While the invention has been described in detail with reference to preferred embodiments thereof, it will be apparent to one skilled in the art that various changes can be made, and equivalents employed, without departing from the scope of the invention.

What is claimed is:

1. A brace for securing accurately related maxillary and mandibular casts while an articulator is attached to the casts, comprising:

a spine having first and second ends;

a first stabilizing pad at the first end of the spine and a second stabilizing pad at the second end of the spine, the first stabilizing pad and the second stabilizing pad each being securable to a wet or moist cast material in order to create a connection between accurately related mandibular and maxillary casts; and a breakaway element in one of the spine, the first stabilizing pad, and second stabilizing pad;

wherein force applied to the spine breaks the connection at said breakaway element.

2. The brace of claim 1, wherein the cast material is a gypsum product.

3. The brace of claim 1 further comprising a tab extending from the spine, the tab providing an area for manipulation of the spine.

4. The brace of claim 3, wherein the tab is coextensive with the spine.

5. The brace of claim 1, comprising two breakaway elements.

6. The brace of claim 1, wherein the breakaway element comprises a necked-down portion of the spine, the necked-down portion located proximate to an area of the spine where the spine is connected to one of the first stabilizing pad and the second stabilizing pad.

7. The brace of claim 1, wherein the spine comprises a widened center portion, and said breakaway element comprises a notch between the first stabilizing pad and said widened center portion.

8. The brace of claim 7 further comprising a tab extending from the spine, the tab being coextensive with the widened center portion of the spine.

9. The brace of claim 1, wherein the spine, the first stabilizing pad, and the second stabilizing pad are integrally formed as one piece.

10. The brace of claim 9 further comprising a tab integral with the spine, the tab providing an area for manipulation.

11. The brace of claim 1 further comprising a maxillary cast and a mandibular cast and wherein the first stabilizing pad and the second stabilizing pad are secured to the casts with a marine adhesive.

12. The brace of claim 1, wherein the first and second stabilizing pads each have a securing side and include an adhesive material on the securing side, the adhesive selected from the group consisting of cyanoacrylates, sticky wax, gray stick compound, impression compound, polyethylene, epoxies including marine epoxies, adhesive tapes, spring adhesives and resins including marine resins.

13. The brace of claim 1 further comprising a maxillary cast having a magnetic element, a mandibular cast having a magnetic element, and wherein the breakaway element comprises magnetic elements in the first and second stabilizing pads, the pad magnetic elements having polarities opposite the cast magnetic elements polarity when the stabilizing pads are secured to the casts.

14. The brace of claim 13, wherein the pad magnetic elements comprise electromagnets and electrical conductors extending from the electromagnets.

15. The brace of claim 13, wherein the pad magnetic elements comprise rare earth or ferrous magnetic elements.

16. The brace of claim 13, wherein the maxillary cast magnetic element and the mandibular cast magnetic element each comprise ferromagnetic elements.

17. A method of temporarily securing accurately related mandibular and maxillary casts, comprising:
    providing a brace including a first stabilizing pad and a second stabilizing pad, the first and second stabilizing pads connected by a spine, the brace including a breakaway element;
    securing the first stabilizing pad to a mandibular cast and the second stabilizing pad to a maxillary cast to create a connection between the accurately related casts; and
    applying a force to the spine to break the connection between the maxillary and mandibular casts at the breakaway feature.

18. The method of claim 17, wherein the securing step includes securing the first stabilizing pad to a wet or moist maxillary cast and securing the second stabilizing pad to a wet or moist mandibular cast.

19. The method of claim 18, wherein the securing step includes securing the first stabilizing pad and the second stabilizing pad to the casts with an adhesive which adheres to wet or moist cast material.

20. The method of claim 19, wherein the cast material is a gypsum product.

21. The method of claim 17, wherein the providing step comprises providing a brace which includes a tab extending from the spine.

22. The method of claim 17, wherein the first stabilizing pad and the second stabilizing pad each include magnetic elements and wherein the maxillary and mandibular casts each include magnetic elements, and wherein the securing step includes securing the magnetic element of the first stabilizing pad to the magnetic element in the maxillary cast and securing the magnetic element of the second stabilizing pad to the magnetic element in the mandibular cast.

23. The method of claim 17, wherein the applying force step includes producing a twisting force on the spine.

24. The method of claim 17, wherein the providing step comprises providing a breakaway element which comprises a necked-down portion of the spine located proximate to one of the stabilizing pads.

25. The method of claim 17, wherein the providing step comprises providing a breakaway element which comprises a notch defined between either the first stabilizing pad and a widened center portion of the spine, between the second stabilizing pad and the widened center portion of the spine, or both.

26. The method of claim 17, wherein in the applying a force step, the connection between the maxillary and mandibular cast is broken such that the first and second stabilizing pads remain secured to the maxillary and mandibular casts.

27. A brace for securing accurately related maxillary and mandibular casts while an articulator is attached to the casts, comprising:
    first stabilizing means and second stabilizing means each being securable to a wet or moist cast material;
    connecting means for connecting the first stabilizing means to the second stabilizing means to create a connection between maxillary and mandibular casts; and
    breakaway means for breaking the connection between the maxillary and mandibular casts when manual pressure is applied to one of the connecting means, the first stabilizing means, or the second stabilizing means.

28. The brace of claim 27, wherein the cast material is a gypsum product.

29. The brace of claim 27, further comprising tab means extending from the rigid connecting means, the tab means for providing an area for manipulating the brace.

30. The brace of claim 27, wherein the breakaway means comprises a necked-down portion of the connecting means, the necked-down portion located proximate to where the connecting means is connected to the first and second stabilizing means.

31. The brace of claim 27, wherein the breakaway means comprises a notch defined between the first stabilizing means and a reinforcing means in the connecting means, between the second stabilizing means and the reinforcing means in the connecting means, or both.

32. The brace of claim 27, wherein the brace includes two breakaway means.

33. The brace of claim 27, further comprising a maxillary cast having a magnetic element, a mandibular cast having a magnetic element, wherein the breakaway means comprises magnetic elements in the first and second stabilizing means which have polarities opposite to the magnetic elements of the maxillary and mandibular casts when the stabilizing pads are secured to the casts.

34. The brace of claim 33, wherein the first and second stabilizing means magnetic elements comprise electromagnets and electrical conductors extending from the electromagnets.

35. The brace of claim 27, wherein the first and second stabilizing means further comprise adhesive means capable of adhering the stabilizing means to wet or moist casting material.

36. A kit for temporarily securing a maxillary cast to a mandibular cast, the kit comprising:
    a brace according to claim 1;
    an adhesive for securing the brace to the casts; and
    a package containing the brace and the adhesive.

37. The kit according to claim 36, further comprising an adhesive applicator.

38. The kit according to claim 36, wherein the adhesive is preapplied to the brace.

* * * * *